(12) United States Patent
Ruan et al.

(10) Patent No.: US 8,469,984 B2
(45) Date of Patent: Jun. 25, 2013

(54) SINGLE USE LANCING DEVICE

(75) Inventors: Tieming Ruan, Randolph, NJ (US);
Mohammad A. Kheiri, Elkhart, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 438 days.

(21) Appl. No.: 12/083,748

(22) PCT Filed: Oct. 23, 2006

(86) PCT No.: PCT/US2006/041315
§ 371 (c)(1),
(2), (4) Date: Jul. 14, 2009

(87) PCT Pub. No.: WO2007/050528
PCT Pub. Date: May 3, 2007

(65) Prior Publication Data
US 2009/0299397 A1    Dec. 3, 2009

Related U.S. Application Data

(60) Provisional application No. 60/729,825, filed on Oct. 25, 2005.

(51) Int. Cl.
*A61B 5/151* (2006.01)
(52) U.S. Cl.
USPC .......................................................... 606/181
(58) Field of Classification Search
USPC ... 606/181–183, 167; 600/583, 573; 604/131, 604/134, 164.08, 152, 136, 130, 192, 137, 604/197, 198, 272
See application file for complete search history.

(56) References Cited

U.S. PATENT DOCUMENTS

| | | | | | |
|---|---|---|---|---|---|
| 5,074,872 | A | * | 12/1991 | Brown et al. | 606/182 |
| 5,133,730 | A | * | 7/1992 | Biro et al. | 606/182 |
| 5,439,473 | A | * | 8/1995 | Jorgensen | 606/182 |
| 5,628,765 | A | * | 5/1997 | Morita | 606/182 |

(Continued)

FOREIGN PATENT DOCUMENTS

| EP | 0 747 006 A1 | 12/1996 |
|---|---|---|
| EP | 0 894 471 A2 | 2/1999 |
| WO | WO 2005/013825 A1 | 2/2005 |

OTHER PUBLICATIONS

Written Opinion corresponding to International Patent Application No. PCT/US2006/041315, European Patent Office, dated Mar. 5, 2007, 8 pages.

(Continued)

*Primary Examiner* — Ryan Severson
*Assistant Examiner* — Rachel S Papeika
(74) *Attorney, Agent, or Firm* — Nixon Peabody LLP (57) ABSTRACT

A lancing device comprises a housing, a trigger button, a drive spring and a protective cap. The housing forms an aperture and an opening opposite thereof. A lancet partially extends through the aperture. The trigger button is located near the opening. At least a portion of the trigger button is external to the housing. The drive spring is attached to and connects the lancet and the trigger button. The drive spring moves the lancet from the cocked position to the puncture position. The protective cap is removeably attached to the lancet opposite the drive spring and engages the housing when the cap is removeably attached to the lancet. The cap prevents the drive spring from moving the lancet to the puncture position prior to removing the cap from the lancet.

22 Claims, 9 Drawing Sheets

U.S. PATENT DOCUMENTS

| | | | | |
|---|---|---|---|---|
| 5,707,384 A | | 1/1998 | Kim | 606/181 |
| 5,741,288 A | * | 4/1998 | Rife | 606/181 |
| 5,755,733 A | * | 5/1998 | Morita | 606/182 |
| 6,042,595 A | * | 3/2000 | Morita | 606/181 |
| 6,136,013 A | * | 10/2000 | Marshall et al. | 606/167 |
| 6,168,606 B1 | | 1/2001 | Levin et al. | 606/181 |
| 6,390,990 B1 | | 5/2002 | Marshall et al. | 600/573 |
| 6,852,119 B1 | | 2/2005 | Abulhaj et al. | 606/182 |
| 2002/0077650 A1 | | 6/2002 | Schraga | 606/182 |
| 2002/0087180 A1 | * | 7/2002 | Searle et al. | 606/181 |
| 2003/0216767 A1 | | 11/2003 | List et al. | 606/181 |
| 2005/0143771 A1 | * | 6/2005 | Stout et al. | 606/181 |
| 2006/0116705 A1 | * | 6/2006 | Schraga | 606/181 |

OTHER PUBLICATIONS

International Search Report corresponding to International Patent Application No. PCT/US2006/041315, European Patent Office, dated Mar. 5, 2007, 5 pages.

* cited by examiner

SINGLE USE LANCING DEVICE

CROSS-REFERENCE TO RELATED APPLICATIONS

This application claims priority to Application No. 60/729,825 filed on Oct. 25, 2005, which is incorporated by reference in its entirety.

FIELD OF THE INVENTION

The present invention relates generally to diagnostic instruments and, more particularly, to a single-use lancing device for obtaining a fluid sample from a test subject.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check their blood glucose levels to regulate the glucose intake in their diets.

One method of obtaining a body fluid sample, such as a whole blood sample, is to use a lancing device. For example, a disposable lancing device may be utilized as a one-time means of collecting a whole blood sample. After the single use lancing device has been utilized, it is then discarded and a second disposable lancing device can be used to obtain a sample at a later time. The whole blood sample may then be used to determine the glucose concentration of an individual.

Existing lancing devices use a lancet to pierce the tissue of the skin, allowing a blood sample to form on the skin's surface. Typically, lancing devices hold the lancet within them when the lancet is not in use, so as to shield the user from injury as well as to assist in preventing or inhibiting contamination. Single use lancing devices are typically purchased in a cocked position, wherein the depression of a firing button or other mechanism causes the lancing device to fire—extending the lancet outside of the lancing device. One problem associated with typical disposable lancing devices is that of premature or accidental firing. When a disposable lancing device is prematurely or accidentally fired, it effectively becomes inoperative (useless) for obtaining a fluid sample. Further, in certain circumstances, the accidental firing can pose a threat of unintended punctures to a user or other individual.

It is intended that a disposable lancing device be discarded after performing a single puncture. Unlike multi-use lancing devices, disposable lancing devices include an attached lancet that can not be removed from the lancing device or replaced. As such, once the lancet has been used to puncture the skin of a test subject, the lancet becomes contaminated by the fluid sample and a new, sanitary lancet cannot be inserted. As such, the reuse of disposable lancing devices can pose various medical and health risks to a user.

Additionally, because single use lancing devices are intended to be utilized once and then discarded, it is desirable to produce the lancing devices at a minimal cost. Currently, disposable lancing devices are not particularly easy to assemble. Standard lancing devices are typically made using a "top down" method that requires numerous components to be assembled—each component requiring a distinct mold for its production. The numerous components are then inserted into a housing that completely surrounds a portion of the components. As such, the size of the lancet, and any protective cap associated therewith must be sufficiently small to extend out of an aperture formed in the housing. Due to this "top down" assembly method, lancets are not easily assembled because the handled components tend to be small and are inserted into the surrounding housing.

It would be desirable to have a disposable lancing device and a method for using the same that addresses these issues.

SUMMARY OF THE INVENTION

A lancing device is disclosed according to one embodiment of the present invention. The lancing device is adapted to move a lancet from a cocked position to a puncture position. The lancing device includes a housing, a trigger button, a drive spring, and a protective cap. The housing forms an aperture and an opening opposite the aperture while the lancet is adapted to partially extend through the aperture in the housing. The trigger button is located near the opening in the housing and the drive spring connects the trigger button to the lancet. The drive spring is adapted to move the lancet from the cocked position to the puncture position through the aperture in the housing. The protective cap engages the housing and is removeably attached to the lancet opposite the drive spring. The protective cap prevents the drive spring from moving the lancet to the puncture position prior to the removal of the protective cap from the lancet.

A method for using a lancing device is disclosed according to one embodiment of the present invention. The method includes the act of providing a lancing device that includes a housing, a lancet, a plurality of cantilevers, a trigger button, and a protective cap. The housing forms an aperture and an opening opposite the aperture while the lancet is adapted to partially extend through the aperture in the housing. The plurality of cantilevers are generally parallel to each other and are located generally adjacent the aperture of the housing. The protective cap engages the housing near the aperture and is removeably attached to the lancet opposite the trigger button. The method further includes the act of rotating the protective cap to detach the protective cap from the housing. The method further includes the act of removing the protective cap from the lancing device causing the lancet to contact the plurality of cantilevers. The method further includes the act of depressing the trigger button to cause the lancet to force the plurality of cantilevers apart from one another thereby allowing the lancet to puncture the skin of a subject.

The above summary of the present invention is not intended to represent each embodiment, or every aspect, of the present invention. Additional features and benefits of the present invention are apparent from the detailed description and figures set forth below.

DESCRIPTION OF ILLUSTRATED EMBODIMENTS

The present invention is directed to a single-use lancing device for obtaining a body fluid sample from a test subject. The body fluid generally contains at least one analyte that may then be examined to determine its concentration in the body fluid sample. For example, this sample may be analyzed with a meter and test strip, or similar devices, to determine the concentration of the analyte to be examined. Examples of the types of analytes that may be collected with a lancing device include glucose, lipid profiles (e.g., cholesterol, triglycerides, LDL and HDL), microalbumin, hemoglobin $A_{1C}$, fructose, lactate, or bilirubin.

Figure 1:
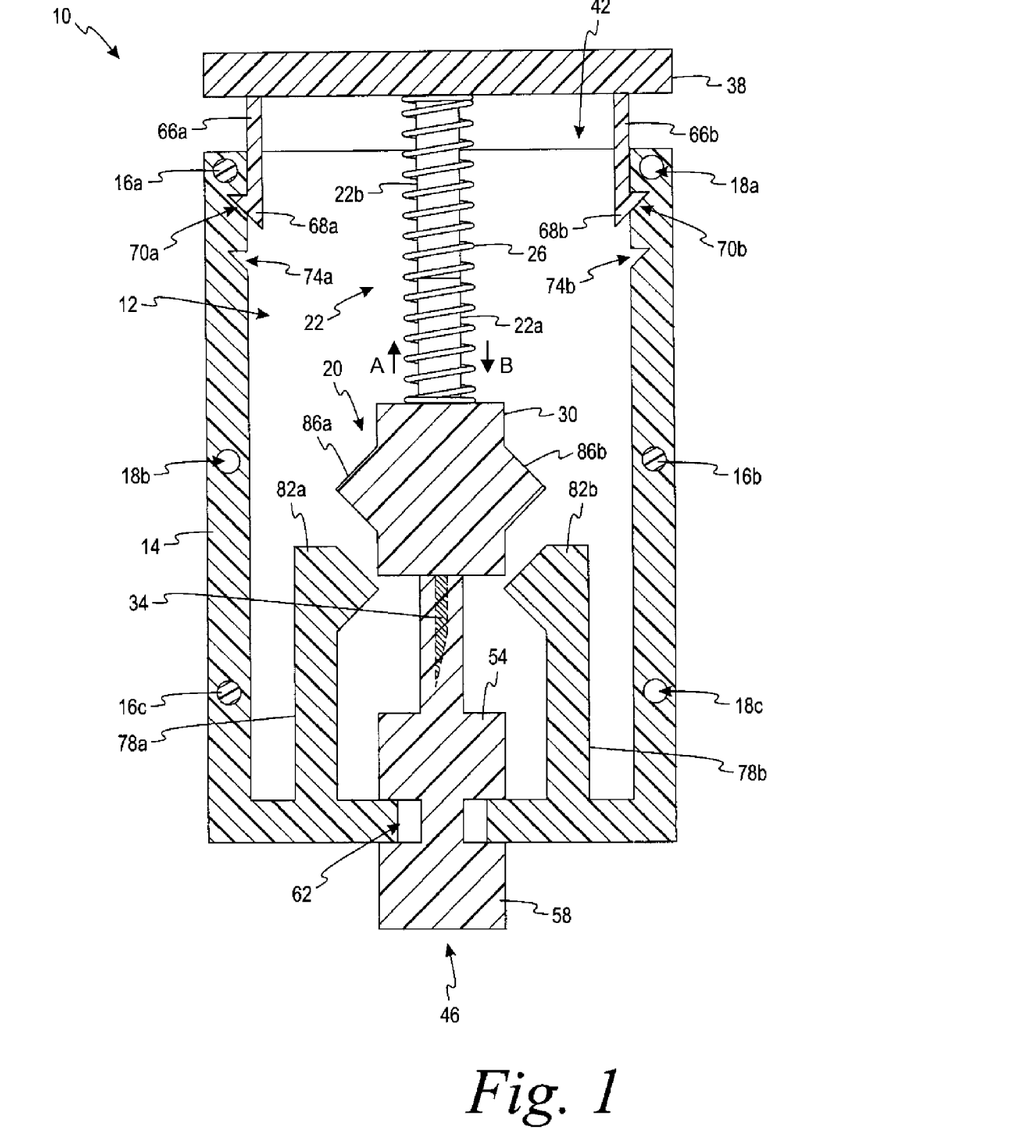
FIG. 1 is a cross-sectional view of a lancing device with a lancing mechanism in a cocked position, according to one embodiment of the present invention.

Turning now to the drawings and initially to FIG. 1, a lancing device 10 for obtaining a fluid sample from a test subject is illustrated, according to one embodiment of the present invention. The lancing device 10 includes a lancing mechanism 12 located within a housing 14 of the lancing device 10. The housing 14 consists of two identical housing halves 114 and 214 (as will be further detailed with respect to FIG. 7). The two housing halves 114, 214 can be attached together using pins 16a-c and holes 18a-c to form the housing 14 of the lancing device 10. The locations of the pins 16a-c and the holes 18a-c are designed so that the pins 16a-c correspond with their reciprocal holes 18a-c when the two housing halves 114, 214 are attached together.

The lancing mechanism 12, located in the housing 14 of the lancing device 10, includes a lancet 20, a shaft 22 having a first portion and a second portion, and a drive spring 26. The lancet 20 is formed by a body 30 with a lance 34 extending therefrom. The lance 34 is adapted to puncture the skin of a test subject when the lancing mechanism 12 is moved from a cocked position (illustrated in FIG. 1) to a puncture position (illustrated in FIG. 5). A first portion of the shaft 22 (e.g., lancet shaft 22a) extends from the body 30 of the lancet 20 opposite the lance 34. A second portion of the shaft 22 (e.g., trigger-button shaft 22b) extends from a trigger button 38 located near an opening 42 formed by the housing 14. The drive spring 26 is adapted to at least partially surround the lancet shaft 22a and the trigger-button shaft 22b. The drive spring 26 is attached to the lancet 20 and the trigger button 38 at opposite ends, and is adapted to move the lancing mechanism 12 from the cocked position to the puncture position and back to a resting position (as illustrated in FIG. 6).

The lance 34 of the lancet 20 is initially at least partially enclosed by a protective cap 46. The protective cap 46 is removably attached to the lancet 20 and extends from the body 30 of the lancet 20 to the exterior of the housing 14. The protective cap 46 extends through an aperture 50 (FIGS. 2a-b) formed in the housing 14 opposite the opening 42. In one embodiment, the protective cap 46 forms a plurality of wings 54, 58 having a slot 62 formed therebetween. The slot 62 is adapted to receive a portion of the housing 14 between the plurality of wings 54, 58. Prior to the removal of the protective cap 46, the inner wing 54 of the protective cap 46 is in contact with the interior of the housing 14 near the aperture 50. The outer wing 58 of the protective cap 46 is located external to the housing 14 and is adapted to be grasped by a user. When the slot 62 of the protective cap 46 is engaged by the housing 14, the protective cap 46 exerts pressure on the lancet 20 in the direction of arrow A—compressing the drive spring 26 and causing the lancet shaft 22a to contact the trigger-button shaft 22b.

Figure 2A:
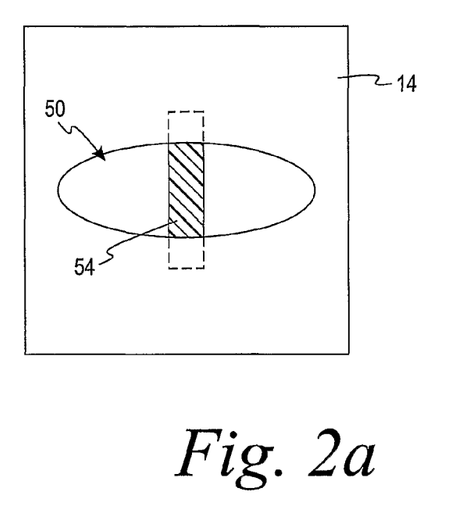
FIG. 2a is an end view of the lancing device of FIG. 1 with a protective cap aligned in a first direction relative to an aperture.
Figure 2B:
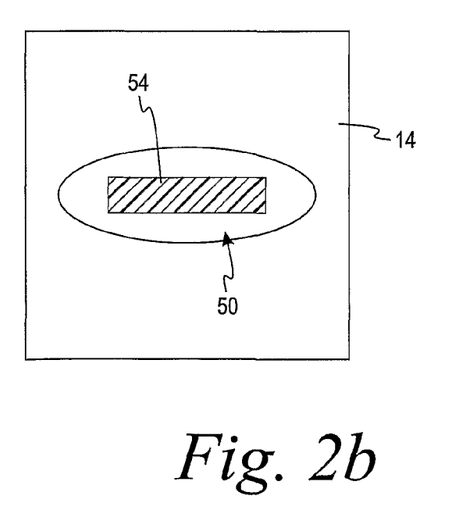
FIG. 2b is an end view of the lancing device of FIG. 1 with the protective cap aligned in a second direction relative to the aperture.

Referring also to FIGS. 2a-b, the aperture 50 of the housing 14 is generally an elongated opening such that the plurality of wings 54, 58 of the protective cap 46 are longer than the aperture 50 in a first direction, while at least the inner wing 54 is shorter than the aperture 50 in a second direction. Thus, when the protective cap 46 is aligned in the first direction (as shown in FIG. 2a) the inner wing 54 engages the housing 14 and the protective cap 46 is not permitted to be removed through the aperture 50. Alternatively, when the protective cap 46 is aligned in the second direction (as shown in FIG. 2b), the inner wing 54 of the protective cap 46 is no longer engaged by the housing 14 and the protective cap 46 may be removed from the housing 14 through the aperture 50, as will be further discussed with respect to FIG. 3. According to one embodiment, the aperture 50 has a substantially oval shape. In other embodiments, the aperture 50 has a substantially rectangular shape. It should be understood that the shape of the aperture 50 can form of any suitable shape that allows the protective cap 46 to be removed from the housing 14 after the protective cap 46 has been rotated to a certain degree.

The protective cap 46, as described above, is adapted to inhibit or prevent the accidental or premature filing of the lancing mechanism 12. As illustrated in FIG. 1, when the housing 14 is engaged by the slot 62 of the protective cap 46, the trigger button 38 is inhibited from being depressed—in the direction of Arrow B—by a user. As discussed above, when the housing 14 is engaged by the slot 62 of the protective cap 46, the drive spring 26 is compressed causing the lancet shaft 22a to contact the trigger-button shaft 22b. This forms a generally rigid structure between the trigger button 38 and the protective cap 46. If accidental pressure is exerted on the trigger button 38 in the direction of Arrow B, the generally rigid structure between the trigger button 38 and the protective cap 46 inhibits further movement of the trigger button 38 due to the engagement of the housing 14 by the slot 62. Thus, the lancing mechanism 12 is prevented from moving from the cocked position to a puncture position prior to the removal of the protective cap 46.

The trigger button 38 is located near the opening 42 of the housing 14 of the lancing device 10. The trigger button 38 is at least partially located external to the housing 14 and is accessible by a user. The trigger button 38 has a plurality of prongs 66a, 66b that extends from the trigger button 38 into the housing 14 of the lancing device 10. Each of the prongs 66a, 66b have a respective barbed end 68a, 68b. As illustrated in FIG. 1, the barbed ends 68a, 68b of the trigger button 38 are initially fitted into a respective starting dent 70a, 70b formed within an inner wall (not shown) of the housing 14 of the lancing device 10. The starting dents 70a-b are adapted to receive all or a portion of the barbed ends 68a-b therein. The barbed ends 68a-b and the starting dents 70a-b are adapted to prevent the trigger button 38 from moving in the direction of Arrow A when the barbed ends 68a-b are received by the starting dents 70a-b. In some embodiments, the location of the starting dents 70*a-b* are such that, when the barbed ends 68*a-b* are received by the starting dents 70*a-b*, the trigger button 38 does not fully enclose the opening 42 in the housing 14.

The housing 14 of the lancing device 10 also contains a plurality of locking dents 74*a*, 74*b* formed within an inner wall (not shown) of the housing 14 of the lancing device 10. The locking dents 74*a-b* are located a predetermined distance from the starting dents 70*a-b* in the direction of arrow B. The shape of the locking dents 74*a-b* are substantially similar to the shape of the starting dents 70*a-b* so that the shape of the barbed ends 68*a-b* of the prongs 66*a-b* of the trigger button 38 are adapted to be received by the locking dents 74*a-b*. The barbed ends 68*a-b* and locking dents 74*a-b* are designed such that, once the barbed ends 68*a-b* of the prongs 66*a-b* are received within the locking dents 74*a-b*, the barbed ends 68*a-b* are essentially trapped and prevent the trigger button 38 from being moved in the direction of Arrow A. In this manner, the locking dents 74*a-b* assist in inhibiting the re-use of the lancing device 10 once the lancing mechanism 12 has moved from the cocked position to the puncture position, as will be further detailed below with respect to FIG. 5.

The lancing device 10 also includes a plurality of cantilevers 78*a*, 78*b* located within the housing 14. The cantilevers 78*a-b* are located near the aperture 50 of the housing 14 and may be formed integrally with the housing 14 or may be inserted into the housing 14 after the housing 14 has been formed. Each of the cantilevers 78*a*, 78*b* have a respective head 82*a*, 82*b* that is adapted to contact one or more protrusion 86*a*, 86*b* extending from the body 30 of the lancet 20. The heads 82*a-b* of the cantilevers 78*a-b* are adapted to engage the respective protrusions 86*a-b* as will be further detailed with respect to FIGS. 3-6.

Figure 3:
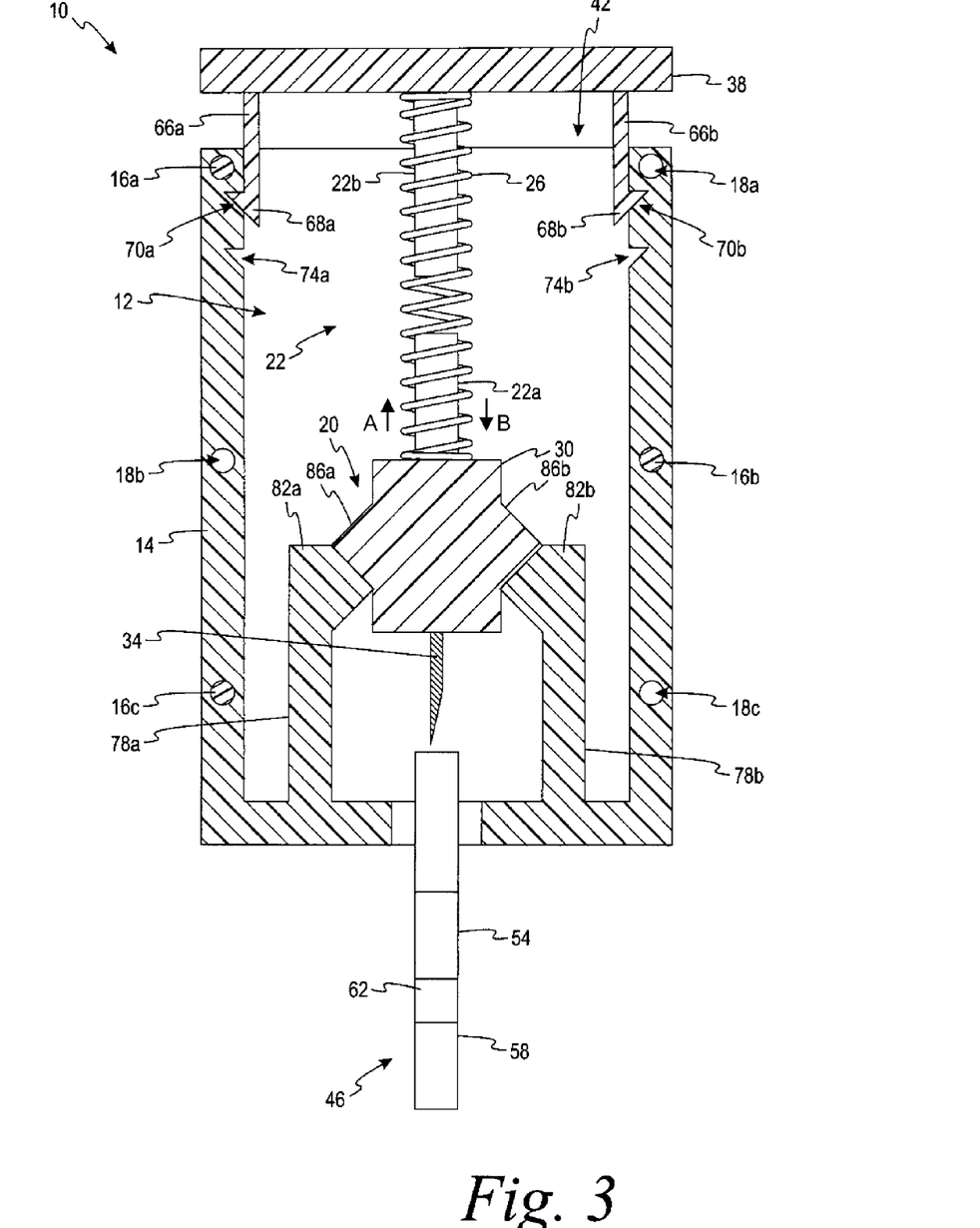
FIG. 3 is a cross-sectional view of the lancing device of FIG. 1 in a partially cocked position upon removal of the protective cap.

Referring also to FIG. 3, the lancing device 10 is illustrated as the protective cap 46 is being removed from the lancet 20, according to one embodiment. To remove the protective cap 46 from the lancet 20, the protective cap 46 is rotated relative to the lancet 20. After the protective cap 46 has been rotated (as illustrated in FIG. 2*b*) and the protective cap 46 may be pulled through the aperture 50 of the lancing device 10 in the direction of Arrow B. The initially compressed drive spring 26 (as shown in FIG. 1) is now allowed to partially decompress and move the lancet 20 in the direction of Arrow B. The lancet 20 continues to move in the direction of Arrow B until the protrusions 86*a-b* of the lancet 20 contact the heads 82*a-b* of the cantilevers 78*a-b*, as illustrated in FIG. 3. The lancing mechanism of the lancing device 10 is now in a partially cocked position. In this position, the drive spring 26 remains partially compressed. Once the protective cap 46 has been removed and the lancing mechanism 12 of the lancing device 10 is in the partially cocked position, the lancing device 10 is ready to be fired to provide a puncture of a test subject's skin.

Figure 4:
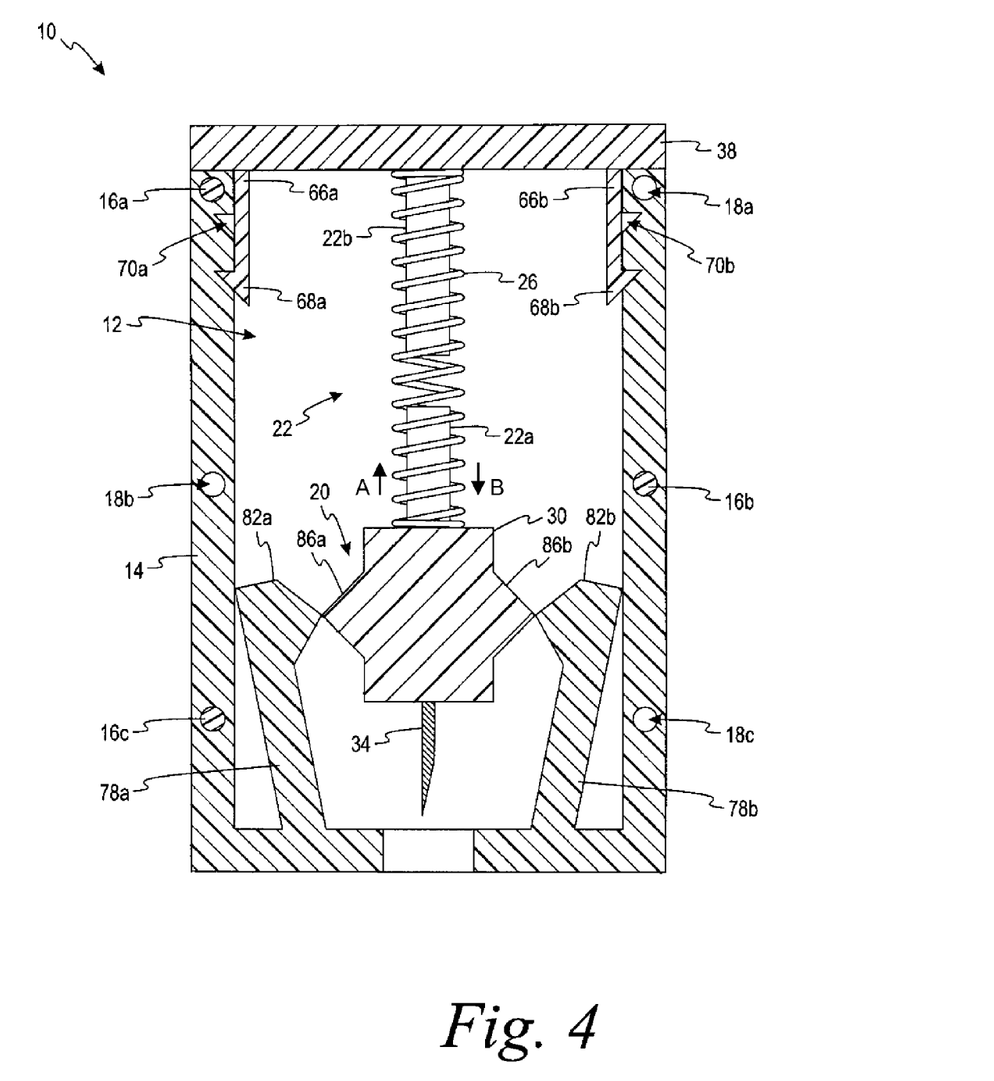
FIG. 4 is a cross-sectional view of the lancing device of FIG. 1 upon depression of a trigger button.

Referring also to FIG. 4, the lancing device 10 is illustrated as the lancing mechanism 12 begins to fire. The lancing mechanism 12 of the lancing device 10 is fired by depressing the trigger button 38 towards the housing 14 in the direction of Arrow B. The force exerted on the drive spring 26 by depressing the trigger button 38 compresses the drive spring 26, thereby exerting an increased force on the lancet 20. The increased force exerted on the lancet 20 causes the lancet 20 to move in the direction of Arrow B, thereby forcing apart the cantilevers 78*a-b* as illustrated in FIG. 4. The cantilevers 78*a-b* are made of a material that enables some deformation while remaining generally prone to their initial position. For example, the cantilevers 78*a-b* may be formed from a polymer material such as polycarbonate or ABS (Acrylonitrile, Butadiene, Styrene). However, other materials such as metals may achieve the desired function and may therefore also be used. As the tips of the protrusions 86*a-b* of the lancet 20 pass the tips of the heads 82*a-b* of the cantilevers 78*a-b*, the cantilevers 78*a-b* no longer prohibit the drive spring 26 from fully decompressing. Additionally, as the tips of the protrusions 86*a-b* of the lancet 20 pass the tips of the heads 82*a-b* of the cantilevers 78*a-b*, the cantilevers 78*a-b* are allowed to spring back to their original positions. Thus, the heads 82*a-b* of the cantilevers 78*a-b* slidably contact the protrusions 86*a-b* of the lancet 20, forcing the lancet 20 in the direction of Arrow B. This sliding contact between the heads 82*a-b* of the cantilevers 78*a-b* and the protrusions 86*a-b* boosts the puncture velocity of the lancet 20 due to the addition of force exerted by the cantilevers 78*a-b*. Both the force exerted on the lancet 20 by the drive spring 26 and the cantilevers 78*a-b* cause the lancing mechanism 12 to move to the puncture position such that the lance 34 extends through the aperture 50 of the lancing device 10. In the puncture position, illustrated in FIG. 5, the lance 34 is capable of piercing the skin of a test subject.

Figure 5:
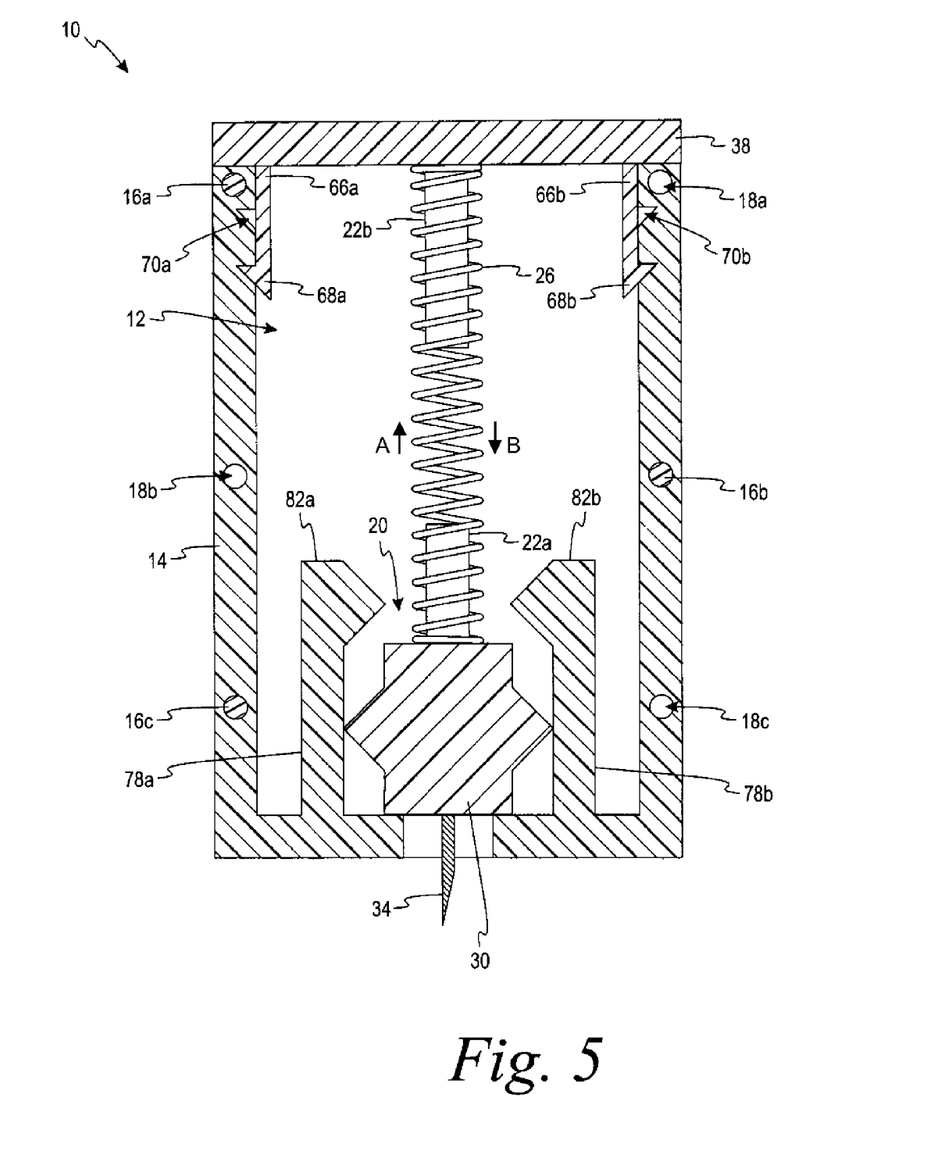
FIG. 5 is a cross-sectional view of the lancing device of FIG. 1 in a puncture position.
Figure 6:
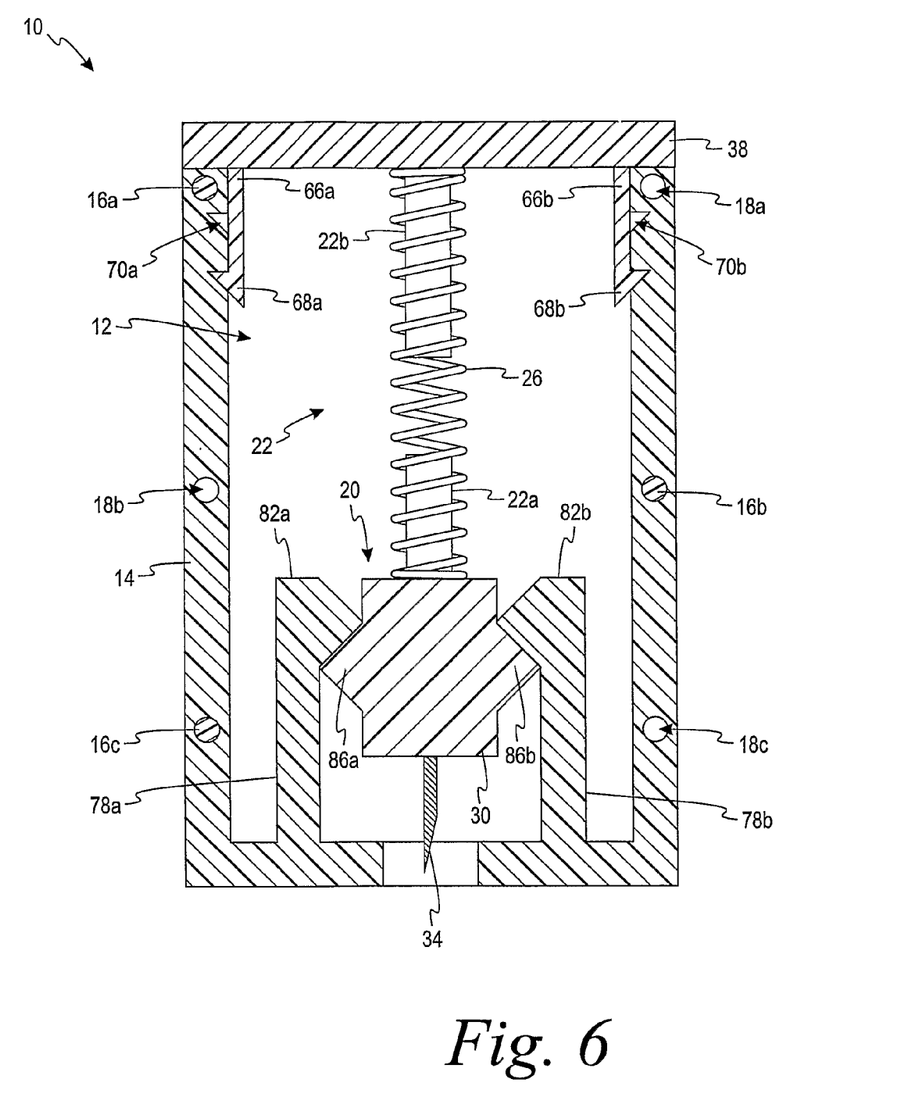
FIG. 6 is a cross-sectional view of the lancing device of FIG. 1 in a resting position.

Referring also to FIG. 5, the lancing mechanism 12 of the lancing device 10 is illustrated in the puncture position, according to one embodiment. As discussed above, once the trigger button 38 is depressed in the direction of Arrow B, the barbed ends 68*a-b* of the prongs 66*a-b* move into the locking dents 74*a-b* formed in the housing 14. As can be seen in FIG. 5, the trigger button 38 is now locked in a position of contact with the housing 14 thereby disabling the trigger button 38 from being depressed more than once. In some embodiments, the prongs 66*a-b* are designed to break free of the trigger button 38 if a user attempts to pull the trigger button 38 away from the housing 14 in the direction of Arrow A. As a result, the lancing device 10 inhibits the reuse of the lancing device 10.

As the lancing mechanism 12 moves from the partially cocked position to the puncture position, the drive spring 26 fully decompresses and the momentum of the lancet 20, along with the additional force applied by the cantilevers 78*a-b* to the lancet 20, cause the drive spring to extend past its resting position. Thus, after the lancing mechanism 12 has reached the puncture position, the lancet 20 is retracted, in the direction of Arrow A, due to the return force of the drive spring 26. Upon retraction, the protrusions 86*a-b* of the lancet 20 contact the heads 82*a-b* of the cantilevers 78*a-b* as the lancet 20 moves in the direction of Arrow A. The contact between the protrusions 86*a-b* and the heads 82*a-b* inhibits the lancet 20 from returning to the partially cocked position, and the lancing mechanism 12 stops in a resting position as illustrated in FIG. 6. In this position, the lance 34 of the lancet 20 is again located within the housing 14. As the protrusions 86*a-b* of the lancet contact the heads 82*a-b* of the cantilevers 78*a-b*, the cantilevers 78*a-b* flex slightly and absorb some of the return force from the drive spring 26. This absorption of some of the force of the drive spring 26 as the drive spring 26 contracts helps to inhibit or prevent multiple punctures of the test subject's skin by the lance 34 of the lancet 20.

Figure 7:
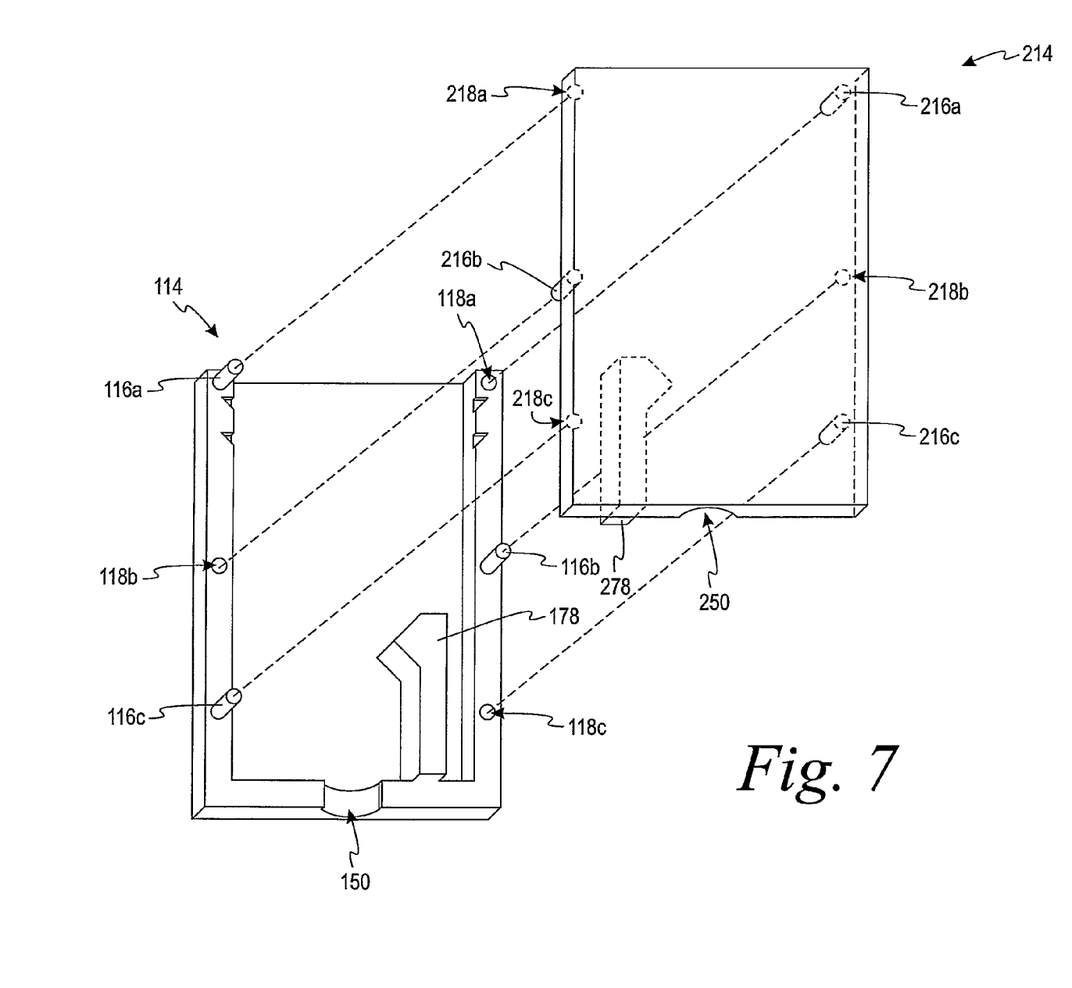
FIG. 7 is a perspective view of a plurality of housing halves adapted to form a housing for a lancing device, according to one embodiment of the present invention.

Turning now to FIG. 7, the assembly of the housing 14 utilizing two housing halves 114 and 214 is illustrated, according to one embodiment. The first housing half 114 includes a plurality of pins 116*a-c* and a plurality of holes 118*a-c* as discussed above. Similarly, the second housing half 214 includes a plurality of pins 216*a-c* and a plurality of holes 218*a-c*. To attach the housing halves 114 and 214, one of the housing halves (e.g., the second housing half 214) is inverted with respect to the other housing half (e.g., the first housing half 114). The two housing halves 114, 214 are attached together—by aligning the pins 116*a-c* with the respective holes 218*a-c* and by aligning the pins 216*a-c* with the holes 118a-c—to form the housing 14 of the lancing device 10. The housing 14 can then be ultrasonically welded to permanently attach the housing halves 114, 214 together. Each of the housing halves 114, 214 includes a respective cantilever 178, 278 located near a respective half aperture 150, 250. The half apertures 150, 250 form the aperture 50 when the housing halves 114, 214 are attached. By utilizing the two identical housing halves 114, 214 to form the housing 14, a single tooling is needed to form the entire housing 14, thereby reducing the manufacturing costs associated with each housing 14.

Figure 8:
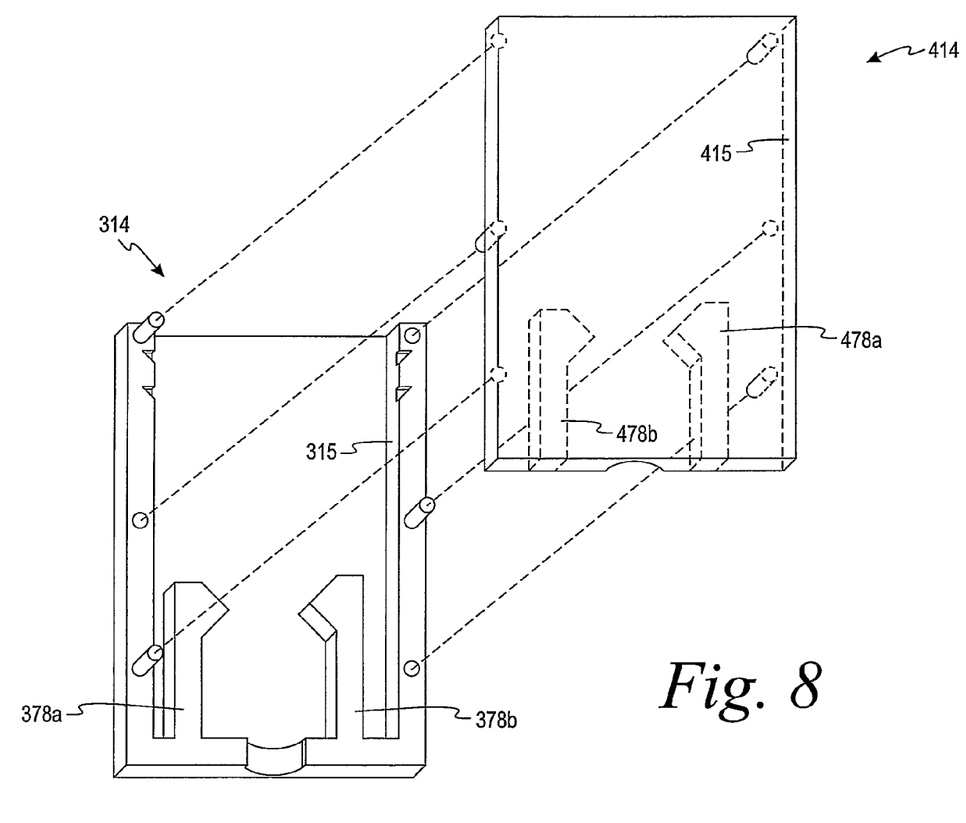
FIG. 8 is a perspective view of a plurality of housing halves adapted to form a housing for a lancing device, according to another embodiment of the present invention.

Turning now to FIG. 8, in other embodiments of the present invention, each of a plurality of housing halves 314, 414 includes a plurality of half cantilevers 378a-b, 478a-b respectively. In these embodiments, the half cantilevers 378a-b, 478a-b are substantially the same depth as the respective inner walls 315, 415 of the housing halves 314, 414. The half cantilevers 378a-b, 478a-b are approximately half the depth of the cantilevers 178 and 278 illustrated in FIG. 7. However, when the housing halves 314, 414 are assembled, the half cantilevers 378a-b formed on the first housing half 314 align with the half cantilevers 478a-b formed on the second housing half 414, to form the cantilevers 78a-b illustrated in FIG. 1. The half cantilevers 378a-b may be attached to the respective half cantilevers 478a-b when the housing halves 314, 414 are attached or may remain separated. However, it should be noted that when the half cantilevers 378a-b, 478a-b remain separated, the four half cantilevers 378a-b, 478a-b continue to function as described above with respect to FIGS. 1-6.

While the above embodiments (FIGS. 7-8) describe the cantilevers being integrally formed along with the housing halves, it should be noted that the cantilevers and the housing halves can be manufactured separately and later assembled. In these embodiments, the housing halves are adapted to receive the cantilevers in a "snap-in" fashion or by another suitable means sufficient to secure the cantilevers to the housing halves. The cantilevers may be added to the housing halves as a pair or one at a time. In still other embodiments, the cantilevers may be added to the housing after the housing halves have been attached.

Figure 9:
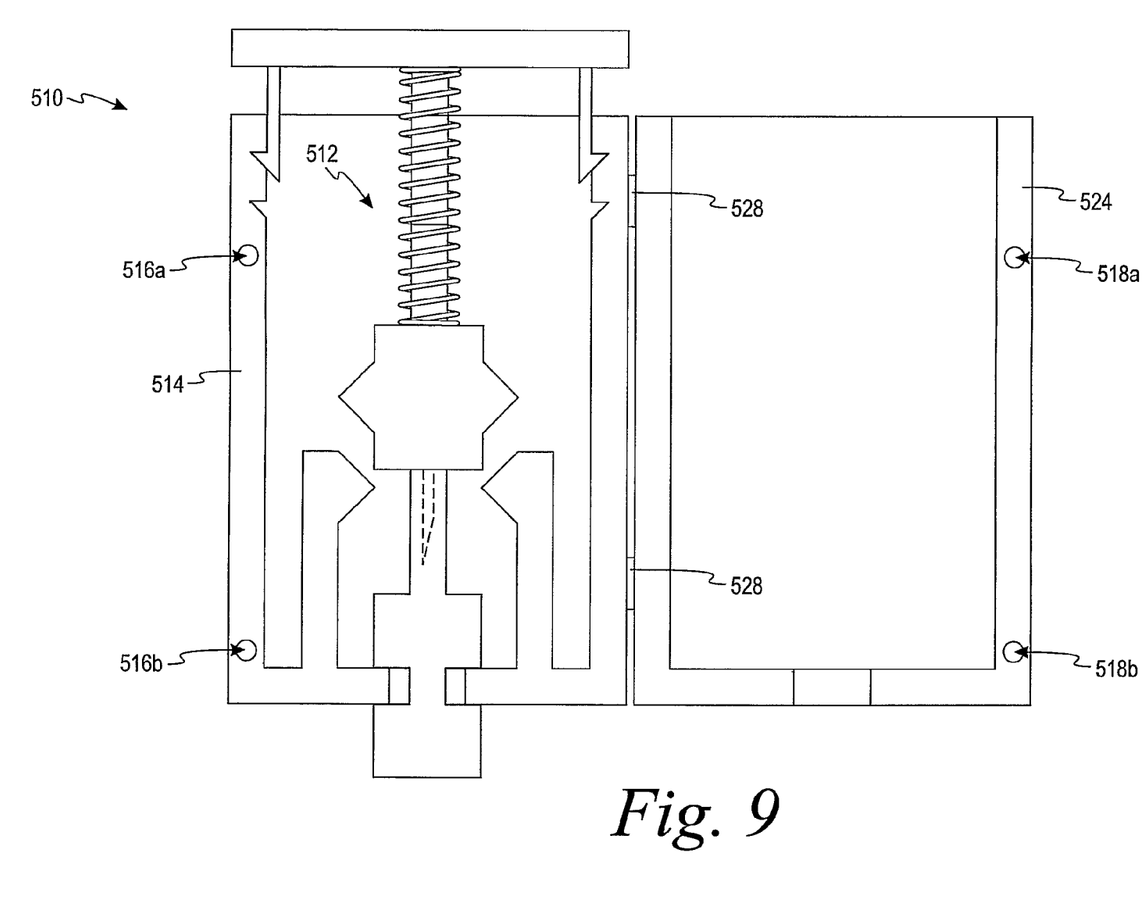
FIG. 9 is a perspective view of a partial housing and a lid adapted to form a housing for a lancing device, according to yet another embodiment of the present invention.

Turning now to FIG. 9, the assembly of a lancing device 510 comprising a partial housing 514 and a lid 524 is illustrated, according to one embodiment. As illustrated in FIG. 9, the lancing mechanism 512 is inserted into the partial housing 514 while the lid 524 remains in an open position. After the lancing mechanism 512 has been inserted, the lid 524 is pivoted on at least one hinge 528 to create the lancing device 510. As illustrated, the partial housing 514 and the lid 524 may include a plurality of pins 516a-b and a plurality of holes 518a-b adapted to assist in the positioning of the lid 524 on the partial housing 514. The lid 524 can be permanently attached to the partial housing 514 via ultrasonic welding or an otherwise suitable technique.

As illustrated above with respect to FIGS. 7-9, the lancing devices of the present invention can be assembled from two housing halves or from a partial housing and a lid. This allows for the lancing mechanism and other internal components to be added to a cavity formed by the housing parts, prior to the housing being enclosed. Presently, disposable lancing devices use a "top-down" method to assemble the lancing device. A "top-down" method of assembly generally refers to the assembly of lancing devices by enclosing the housing of the lancing device prior to adding the rest of the components to the housing. For example, the lancet, spring, and any protective cap are all installed through the "top" (e.g., an opening end) of the lancing device towards the "bottom" (e.g., an aperture end) to assemble the lancing device. Additionally, when a protective cap is utilized on the lancet, the protective cap must be sufficiently small to fit through an aperture at the "bottom" end of the housing. As such, when it is desirable for a portion of the protective cap to be larger than the aperture as described in the above embodiments, the above described assembly methods will typically be employed as opposed to a top-down method of assembly. As such, these methods allow the protective cap, and more specifically the external portion of the protective cap, to be larger in size and, therefore easier to grasp and remove by the user.

Alternative Embodiment A

A lancing device adapted to move a lancet from a cocked position to a puncture position, the lancing device comprising:

a housing forming an aperture and an opening opposite the aperture, the lancet being adapted to partially extend through the aperture in the housing;

a trigger button located near the opening of the housing, at least a portion of the trigger button being external to the housing;

a drive spring attached to and connecting the lancet and the trigger button, the drive spring being adapted to move the lancet from the cocked position to the puncture position; and a protective cap removeably attached to the lancet opposite the drive spring, the protective cap engaging the housing when the protective cap is removeably attached to the lancet, wherein the protective cap prevents the drive spring from moving the lancet to the puncture position prior to removal of the protective cap from the lancet.

Alternative Embodiment B

The lancing device of Alternative Embodiment A, further comprising a plurality of cantilevers located generally parallel to each other, each of the plurality of cantilevers having a head, each of the heads of the cantilevers being adapted to engage the lancet after the protective cap is removed from the lancet.

Alternative Embodiment C

The lancing device of Alternative Embodiment B, wherein the plurality of cantilevers is adapted to inhibit movement of the lancet to the puncture position prior to the trigger button being moved in the direction of the housing.

Alternative Embodiment D

The lancing device of Alternative Embodiment C, wherein the cantilevers assist in moving the lancet to the puncture position once the trigger button is moved in the direction of the housing.

Alternative Embodiment E

The lancing device of Alternative Embodiment C, wherein the cantilevers are further adapted to engage the lancet as the lancet moves from the puncture position to a resting position.

Alternative Embodiment F

The lancing device of Alternative Embodiment A, wherein the aperture formed in a first end of the housing is longer in a second direction than in a first direction.

Alternative Embodiment G

The lancing device of Alternative Embodiment F, wherein the aperture formed in the first end of the housing is generally elliptically shaped

Alternative Embodiment H

The lancing device of Alternative Embodiment F, wherein the aperture formed in the first end of the housing is generally rectangular shaped.

Alternative Embodiment I

The lancing device of Alternative Embodiment A, wherein the housing is formed by two substantially identical housing halves.

Alternative Embodiment J

The lancing device of Alternative Embodiment A, wherein the housing is formed by a partial housing and a lid, the lid being attached to the partial housing by one or more hinges, the partial housing forming a central cavity, wherein the lancet, the drive spring, and a portion of the protective cap are located within the central cavity.

Alternative Embodiment K

The lancing device of Alternative Embodiment A, wherein the trigger button includes a plurality of prongs extending therefrom, each of the plurality of prongs having a barbed end opposite the trigger button, each of the barbed ends being adapted to be received by a locking dent formed in the housing.

Alternative Embodiment L

The lancing device of Alternative Embodiment K, wherein the locking dents are adapted to prevent the lancing device from being reused after the trigger button has been depressed.

Alternative Process M

A method for using a lancing device comprising the acts of:
providing a housing, a lancet, a plurality of cantilevers, a trigger button, and a protective cap, the housing forming an aperture and an opening opposite the aperture, the lancet being adapted to partially extend through the aperture in the housing, the plurality of cantilevers being located generally parallel to each other adjacent the aperture of the housing, the protective cap being removeably attached to the lancet opposite the trigger button, the protective cap engaging the housing when the protective cap is removeably attached to the lancet;
rotating the protective cap to detach the protective cap from the lancet;
removing the protective cap from the lancing device through the aperture, the removal of the protective cap causing the lancet to contact the plurality of cantilevers; and
depressing the trigger button to cause the lancet to force the plurality of cantilevers apart from one another, the separation of the cantilevers allowing the lancet to move to a puncture position.

Alternative Process N

The method of Alternative Process M, wherein the plurality of cantilevers is adapted to assist in moving the lancet to the puncture position after the trigger button has been depressed.

Alternative Process O

The method of Alternative Process M, wherein the trigger button includes a plurality of prongs extending therefrom, each of the plurality of prongs having a barbed end opposite the trigger button, each of the barbed ends being adapted to be received by a locking dent formed in the housing.

Alternative Process P

The method of Alternative Process O, further comprising the act of inhibiting the lancing device from being reused by retaining the barbed ends within the locking dents after the barbed ends have been received therein.

Alternative Process Q

The method of Alternative Process M, further comprising the act of enclosing the housing after the lancet, the plurality of cantilevers, and a portion of the protective cap are inserted therein.

Alternative Process R

The method of Alternative Process Q, wherein the housing is formed by two substantially identical housing halves.

Alternative Process S

The method of Alternative Process Q, where the housing is formed by a partial housing and a lid, the lid being attached to the partial housing by one or more hinges.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:
1. A lancing device adapted to move a lancet from a cocked position to a puncture position, the lancing device comprising:
a housing including an extension forming at least a portion of an aperture at a first end of the housing and an opening opposite the aperture, the lancet being adapted to partially extend through the aperture in the housing;
a trigger button located near the opening of the housing, at least a portion of the trigger button being external to the housing;
a drive spring attached to the lancet and the trigger button, the drive spring being adapted to move the lancet from the cocked position to the puncture position;
a protective cap extending through the aperture and removably attached to the lancet opposite the drive spring, the protective cap configured to be rotated from a first position to a second position, the protective cap including a slot extending inwardly from an outermost surface of the protective cap, the extension extending at least partially into the slot when the protective cap is in the first position thereby allowing the extension to engage the protective cap and prevent the drive spring from moving the lancet to the puncture position, the extension removed from the slot when the protective cap is rotated from the first position to the second position thereby allowing the protective cap to be removed from the lancet; and a plurality of partially deformable cantilevers, the plurality of cantilevers being located generally parallel to each other and extending into the housing from the extension at the first end of the housing, each of the plurality of cantilevers having a head, each of the heads of the cantilevers being adapted to engage the lancet after the protective cap is removed.

2. The lancing device of claim 1, wherein the plurality of cantilevers is adapted to inhibit movement of the lancet to the puncture position prior to the trigger button being moved in the direction of the housing.

3. The lancing device of claim 2, wherein the cantilevers assist in moving the lancet to the puncture position once the trigger button is moved in the direction of the housing.

4. The lancing device of claim 2, wherein the cantilevers are further adapted to engage the lancet as the lancet moves from the puncture position to a resting position thereby allowing the absorption of at least a portion of a return force from the drive spring.

5. The lancing device of claim 1, wherein the aperture formed in a first end of the housing is longer in a second direction than in a first direction.

6. The lancing device of claim 5, wherein the aperture formed in the first end of the housing is generally elliptically shaped.

7. The lancing device of claim 5, wherein the aperture formed in the first end of the housing is generally rectangular shaped.

8. The lancing device of claim 1, wherein the housing is formed by two substantially identical housing halves.

9. The lancing device of claim 1, wherein the housing is formed by a partial housing and a lid, the lid being attached to the partial housing by one or more hinges, the partial housing forming a central cavity, wherein the lancet, the drive spring, and a portion of the protective cap are located within the central cavity.

10. The lancing device of claim 1, wherein the trigger button includes a plurality of prongs extending therefrom, each of the plurality of prongs having a barbed end, each of the barbed ends being adapted to be received by a locking dent formed in the housing.

11. The lancing device of claim 10, wherein each of the barbed ends is initially fitted into a respective starting dent formed in the housing.

12. The lancing device of claim 10, wherein the locking dents are adapted to prevent the lancing device from being reused after the trigger button has been depressed.

13. The lancing device of claim 1, wherein at least one of the plurality of cantilevers is generally perpendicular to the extension forming at least a portion of the aperture.

14. The lancing device of claim 1, wherein one or more of the plurality of cantilever members are integral with the housing.

15. The lancing device of claim 1, wherein the cantilevers are further adapted to engage the lancet as the lancet moves from the puncture position to a resting position thereby allowing the absorption of at least a portion of a return force from the drive spring.

16. A method for using a lancing device comprising the acts of:

providing a housing, a lancet, a plurality of partially deformable cantilevers, a trigger button, and a protective cap configured to be rotated from a first position to a second position, the housing including an extension forming at least a portion of an aperture at the first end of the housing and an opening opposite the aperture, the lancet being adapted to partially extend through the aperture in the housing, the plurality of cantilevers being located generally parallel to each other adjacent the aperture of the housing and extending into the housing from the extension, the protective cap being removably attached to the lancet opposite the trigger button, the protective cap including a slot extending inwardly from an outermost surface of the protective cap, the extension extending at least partially into the slot when the protective cap is in the first position thereby allowing the extension to engage the protective cap;

rotating the protective cap from the first position to the second position thereby disengaging the extension from the protective cap;

removing the protective cap from the lancing device through the aperture, the removal of the protective cap causing the lancet to contact the plurality of cantilevers; and depressing the trigger button to cause the lancet to force the plurality of cantilevers apart from one another, the separation of the cantilevers allowing the lancet to move to a puncture position.

17. The method of claim 16, wherein each of the plurality of cantilevers includes a head and where each of the heads of the cantilevers are adapted to engage the lancet after the protective cap is removed.

18. The method of claim 16, wherein the trigger button includes a plurality of prongs extending therefrom, each of the plurality of prongs having a barbed end, each of the barbed ends being adapted to be received by a locking dent formed in the housing.

19. The method of claim 18, further comprising the act of inhibiting the lancing device from being reused by retaining the barbed ends within the locking dents after the barbed ends have been received therein.

20. The method of claim 16, further comprising the act of enclosing the housing after the lancet, the plurality of cantilevers, and a portion of the protective cap are inserted therein.

21. The method of claim 20, wherein the housing is formed by two substantially identical housing halves.

22. The method of claim 20, wherein the housing is formed by a partial housing and a lid, the lid being attached to the partial housing by one or more hinges.

\* \* \* \* \*